United States Patent
Decker et al.

(10) Patent No.: US 6,673,963 B2
(45) Date of Patent: Jan. 6, 2004

(54) PROCESS FOR PREPARING SORBIC ACID BY THERMAL CLEAVAGE

(75) Inventors: Daniel Decker, Sulzbach (DE); Guenter Roscher, Kelkheim (DE); Christoph Mollenkopf, Frankfurt (DE); Erwin Weiss, Hofheim (DE); Stefan Purps, Koenigstein (DE)

(73) Assignee: Nutrinova Nutrition Specialties & Food Ingredients GmbH, Wiesbaden (DE)

( * ) Notice: Subject to any disclaimer, the term of this patent is extended or adjusted under 35 U.S.C. 154(b) by 0 days.

(21) Appl. No.: 10/237,336

(22) Filed: Sep. 9, 2002

(65) Prior Publication Data

US 2003/0060658 A1 Mar. 27, 2003

(30) Foreign Application Priority Data

Sep. 21, 2001 (DE) .......................................... 101 46 661

(51) Int. Cl.$^7$ .............................................. C07C 57/10
(52) U.S. Cl. ....................................................... 562/601
(58) Field of Search ........................................... 562/601

(56) References Cited

U.S. PATENT DOCUMENTS 3,461,158 A * 8/1969 Hornig et al.

FOREIGN PATENT DOCUMENTS

| DE | 1 042 573 | 11/1958 | ........... C07C/51/09 |
| DE | 1 059 899 | 6/1959 | ........... C07C/51/09 |
| DE | 1 282 645 | 12/1964 | ........... C07C/51/09 |

* cited by examiner

Primary Examiner—Johann Richter
Assistant Examiner—Paul A. Zucker
(74) Attorney, Agent, or Firm—ProPat, L.L.C.

(57) ABSTRACT

The invention relates to a process for preparing sorbic acid by thermal cleavage in a solvent of the polyester prepared from crotonaldehyde and ketene, the cleavage of the polyester being carried out in the presence of 20 to 100% by weight of a secondary or tertiary aliphatic, alicyclic nitrogen- and/or oxygen-containing amine, or aliphatic-aromatic substituted amine, as catalyst.

4 Claims, No Drawings

PROCESS FOR PREPARING SORBIC ACID BY THERMAL CLEAVAGE

BACKGROUND OF THE INVENTION

The invention relates to a process for preparing sorbic acid. Various processes are known for preparing sorbic acid. A particularly economical process starts from the polymeric reaction product polyester which is prepared by reacting crotonaldehyde with ketene in the presence of a fatty acid salt of a divalent and/or trivalent metal of subgroup II to VIII of the Periodic Table of the Elements as catalyst (DE-A 1 042 573). The catalysts are generally used at 0.1 to 5%, preferably at 0.5 to 2%, of the rate of crotonaldehyde used. The polyester thus prepared can be converted into sorbic acid in various ways.

An industrially important process consists, for example, of the thermal catalytic cleavage of the polyester, the polyester being cleaved in an inert diluent which boils at above 150° C. at atmospheric pressure (DE-A 1 059 899) in the presence of a secondary or tertiary aliphatic amine as catalyst at temperatures of 160 to 220° C., simultaneously distilling off the sorbic acid and the solvent (DE-A, 1 282 645). The polyester is cleaved in the presence of 0.5 to 10, preferably 2 to 5, percent by weight of the catalyst amine. In the patent publication (DE-B 1 282 645), it is further maintained that a still greater amount of amine does not lead to a higher yield.

BRIEF DESCRIPTION OF THE INVENTION

The invention relates to a process for preparing sorbic acid by thermal cleavage in a solvent of the polyester prepared from crotonaldehyde and ketene, which comprises cleaving the polyester in the presence of 20 to 100% by weight, based on the polyester used, of a secondary or tertiary aliphatic, alicyclic nitrogen- and/or oxygen-containing or aliphatic-aromatic substituted amine boiling at atmospheric pressure above 100° C., preferably above 150° C., as catalyst.

DETAILED DESCRIPTION OF THE INVENTION

Surprisingly, it has been found that in the thermal cleavage of the polyester as described in DE-A 1 282 645, other than as described there, an abrupt increase in yield of sorbic acid is found when the concentration of the catalyst amine is selected to be at least twice as high as the concentration upper limit specified in DE-A 1 282 645. As described in DE-A 1 282 645, a slight further increase in the amount of amine above the upper amount of catalyst specified there does not lead to significant effect on the sorbic acid yield. Only a great increase in amine concentration leads to significant increase in yield.

Advantageously, the polyester is cleaved in an inert solvent which boils, at atmospheric pressure, above 150° C., preferably above 180° C., the mixture being heated to temperatures of 150 to 300° C., preferably to 270° C. (DE-A 1 059 899). The solvent is generally used in 1 to 15 times the amount by weight, based on the polyester. The thermal cleavage of the polyester advantageously takes place in the presence of 20%, preferably 20 to 60%, of a secondary or tertiary aliphatic, alicyclic, 5- or 6-membered heterocyclic nitrogen- and/or oxygen-containing or aliphatically aromatically substituted amine boiling at atmospheric pressure above 100° C., preferably above 150° C., as catalyst at temperatures of 160 to 220° C., simultaneously distilling off the sorbic acid and the solvent.

Suitable amines which may be mentioned by way of example are: methyloctadecylamine, dimethyloctadecylamine, dimethylhexadecylamine, dimethyltetradecylamine, dimethyldodecylamine, dibutyidodecylamine, N,N',N,N'-tetramethylhexamethylenediamine, N,N,N'-trimethyl-N'-phenylethylenediamine, N-octadecylpyrrolidone, N-octadecylpiperidine, N-dodecylmorpholine, N,N'-dipropylpiperazine, α-hexylpyrrolidone, triethylenetetramine, ethylbis(β-ethylaminoethyl)amine, 1-octyldiethylenetriamine, ethylene glycol bis(2-methylaminoethyl ether), dioctadecylamine, diethylenetriamine, trioctadecylamine, trioctylamine, tricyclohexylamine.

To carry out the reaction, suitable diluents are aliphatic, alicyclic or aromatic hydrocarbons, their chlorine, bromine and nitro derivatives, and also ethers and silicone oils whose boiling point at atmospheric pressure is above 150° C., preferably above 180° C. However, ketones, esters, carboxylic acids and alcohols of the appropriate boiling range can also be used as diluents, although in general the results are not quite as good, since they apparently partly react with the reaction mixture. It is expedient to use those diluents or solvents which are liquid at ambient temperatures, boil at atmospheric pressure below 300° C., preferably below 270° C. and form azeotropic mixtures with sorbic acid, so that they can also act as an entrainer, such as petroleum fractions, dodecane, tetradecane, 5-methyidodecane, dodecene, dicyclohexylmethane, p-di-tert-butylbenzene, 1-methylnaphthalene, 2-methylnaphthalene, 1-ethyinaphthalene, tetrahydronaphthalene, biphenyl, naphthalene, halogenated aliphatic, cycloaliphatic or aromatic hydrocarbons, such as dichlorododecane, 1,5-dibromopentane, benzotrichloride, o- and m-dibromobenzene, nitro compounds such as nitrobenzene, 2-nitrotoluene, nitriles such as benzyl cyanide, carbonyl compounds such as acetophenone or the heterocyclic 2-acetylthiophene, heterocyclic compounds such as chromane, thiophene, ethers such as resorcinol dimethyl ether, diphenyl ether, safrole, isosafrole, acids such as enanthic acid, α-ethylcaproic acid, caprylic acid, capric acid, esters such as ethyl benzoate, methyl phenylacetate and methyl salicylate (DE-A-1 059 899).

The examples below illustrate the invention. The starting material used is a polyester-containing reaction product which is obtained in a similar manner to German published application 1 042 573, example 1. In this case, 420 g of ketene are introduced into a stirred mixture of 800 g of crotonaldehyde, 1200 ml of toluene and 14.2 g of zinc isovalerate at a temperature between 25 and 35° C. The excess crotonaldehyde and toluene are removed in vacuo. The residue obtained is 1150 g of polyester in the form of a high-viscosity brown liquid. In addition to the zinc content of 3000 ppm, this reaction product still has contents which cannot be converted into hexadienoic acids, such as diketene polymers and crotonaldehyde resins.

The fraction convertible into hexadienoic acids was determined by basic saponification of a solution of 60 g of sorbic polyester in 120 g of toluene by 33 g of potassium hydroxide in 260 g of water at room temperature. This produces in the aqueous phase potassium sorbate and the potassium salt of 3-hydroxy-4-hexenoic acid, from which hexadienoic acid can be obtained by acidification. By means of quantitative determination of the two reaction products using HPLC, the polyester fraction convertible into hexadienoic acids can be determined. By means of these mild conditions, the polyester content may be determined very much more precisely than as described in DE-B 1 282 645. Thus the fraction of the crude polyester which is convertible to hexadienoic acids is 89 to 90%, and not, as assumed in DE-B 1 282 645, only 80%. The yields achieved in DE-B 1 282 645 must therefore be corrected, see comparative example 1.

EXAMPLES

Comparative Example 1

A mixture of 100 g of polyester, 200 g of triethylene glycol diethyl ether and 2 g of dimethyloctadecylamine is slowly added dropwise from a dropping funnel into a two-neck flask which is in a heating bath at 220° C. Via a distillation head, the sorbic acid and entrainer are distilled off at about 20 mmHg and liquefied in the receiver. After crystallization, 76 g of pure sorbic acid are obtained. This corresponds to a yield of 76%, based on the crude polyester used. Based on the pure polyester, that is solely taking into account the fraction of 90% which is cleavable to form hexadienoic acids, a yield of 84.4% is then calculated.

Comparative Example 2

A mixture of 100 g of polyester, 200 g of triethylene glycol diethyl ether and 3 g of dimethyloctadecylamine is slowly added dropwise from a dropping funnel into a two-neck flask which is in a heating bath at 220° C. Via a distillation head, the sorbic acid and the entrainer are distilled off at about 20 mmHg and liquefied in the receiver. After crystallization, 76.3 g of pure sorbic acid are obtained. This corresponds to a yield of 76.3%, based on the crude polyester used. Based on the pure polyester, that is solely taking into account the fraction of 90% which is cleavable to form hexadienoic acids, a yield of 84.7% is then calculated.

Example 3

A mixture of 100 g of polyester, 200 g of triethylene glycol diethyl ether and 13 g of dimethyloctadecylamine is slowly added dropwise from a dropping funnel into a two-neck flask which is charged with 30 g of dimethyloctadecylamine and is in a heating bath at 220° C. Via a distillation head, the sorbic acid and the entrainer are distilled off at about 20 mmHg and liquefied in the receiver. After crystallization, 83 g of pure sorbic acid are obtained. This corresponds to a yield of 83%, based on the crude polyester used. Based on the pure polyester, that is solely taking into account the fraction of 90% which is cleavable to form hexadienoic acids, a yield of 92.8% is then calculated.

Example 4

A mixture of 100 g of polyester and 400 g of 2-ethylhexanoic acid is slowly added dropwise from a dropping funnel into a two-neck flask which is charged with 45 g of dimethyloctadecylamine and is in a heating bath at 220° C. Via a distillation head, the sorbic acid and the entrainer are distilled off at about 20 mmHg and liquefied in the receiver. After crystallization, 84.5 g of pure sorbic acid are obtained. This corresponds to a yield of 84.5% based on the crude polyester used. Based on the pure polyester, that is solely taking into account the fraction of 90% which is cleavable to form hexadienoic acids, a yield of 93.9% is then calculated.

Example 5

A mixture of 100 g of polyester, 200 g of triethylene glycol diethyl ether and 13 g of dimethyltetradecylamine is slowly added dropwise from a dropping funnel into a two-neck flask which is charged with 60 g of dimethyloctadecylamine and is in a heating bath at 220° C. Via a distillation head, the sorbic acid and the entrainer are distilled off at about 20 mmHg and liquefied in the receiver. After crystallization, 86 g of pure sorbic acid are obtained. This corresponds to a yield of 86%, based on the crude polyester used. Based on the pure polyester, that is solely taking into account the fraction of 90% which is cleavable to form hexadienoic acids, a yield of 95.5% is then calculated.

What is claimed is:

1. A process for preparing sorbic acid by thermal cleavage in a solvent, of the polyester prepared from crotonaldehyde and ketene, which comprises cleaving the polyester in the presence of about 20 to about 100% by weight based on the polyester used of a secondary or tertiary aliphatic or alicyclic nitrogen- or oxygen- or nitrogen- and oxygen-containing amine or an aliphatic-aromatic substituted amine, acting as catalyst, the amine boiling at atmospheric pressure above about 100° C.

2. The process as claimed in claim 1, wherein about 20 to about 60% by weight based on the polyester used of the amine is used.

3. The process as claimed in claim 1, wherein the amine is selected from one or more of the following compounds:

methyloctadecylamine, dimethyloctadecylamine, dimethylhexadecylamine, dimethyltetradecylamine, dimethyldodecylamine, dibutyidodecylamine, N,N',N,N'-tetramethylhexamethylenediamine, N,N,N'-trimethyl-N'-phenylethyltetradecylamine, N-octadecylpyrrolidone, N-octadecylpiperidine, N-dodecylmorpholine, N,N'-dipropylpiperazine, α-hexylpyrrolidone, triethylenetetramine, ethylbis(β-ethylaminoethyl)amine, 1-octyldiethylenetriamine, ethylene glycol bis-(2-methylaminoethyl ether), dioctadecylamine, diethylenetriamine, trioctadecylamine, trioctylamine and tricyclohexylamine.

4. The process as claimed in claim 1, wherein the polyester, to prepare sorbic acid, is cleaved at temperatures of about 160 to about 220° C., simultaneously distilling off the sorbic acid.

* * * * *